United States Patent
Fernandes et al.

(10) Patent No.: US 10,711,248 B2
(45) Date of Patent: Jul. 14, 2020

(54) DEVICE AND METHOD FOR STANDARDIZING MYOBLAST DIFFERENTIATION INTO MYOTUBES

(71) Applicant: Cytoo, Grenoble (FR)

(72) Inventors: Mathieu Fernandes, Saint-Jean de Moirans (FR); Sebastien Degot, Grenoble (FR); Yoran Margaron, Voiron (FR); Jie Liu, Grenoble (FR); Michel Bornens, Sceaux (FR); Maria Luisa Calvo Munoz, Grenoble (FR); Aurelie Berthelot, Echirolles (FR); Alexandra Fuchs, Beaulieu (FR); Joanne Young, Voreppe (FR); Delphine Morales, Grenoble (FR)

(73) Assignee: CYTOO, Grenoble (FR)

( * ) Notice: Subject to any disclaimer, the term of this patent is extended or adjusted under 35 U.S.C. 154(b) by 0 days.

(21) Appl. No.: 15/105,548

(22) PCT Filed: Dec. 17, 2014

(86) PCT No.: PCT/EP2014/078129
§ 371 (c)(1),
(2) Date: Jun. 16, 2016

(87) PCT Pub. No.: WO2015/091593
PCT Pub. Date: Jun. 25, 2015

(65) Prior Publication Data
US 2016/0312187 A1    Oct. 27, 2016

(30) Foreign Application Priority Data

Dec. 18, 2013   (EP) ..................... 13306759
May 27, 2014   (EP) ..................... 14305785

(51) Int. Cl.
| | | |
|---|---|---|
| C12N 5/077 | (2010.01) | |
| C12M 3/00 | (2006.01) | |
| C12M 1/12 | (2006.01) | |
| C12M 1/00 | (2006.01) | |
| C12M 1/34 | (2006.01) | |
| G01N 15/14 | (2006.01) | |
| G01N 33/50 | (2006.01) | |
| G01N 15/00 | (2006.01) | |
| G01N 15/10 | (2006.01) | |

(52) U.S. Cl.
CPC ........... *C12N 5/0658* (2013.01); *C12M 21/08* (2013.01); *C12M 23/04* (2013.01); *C12M 23/20* (2013.01); *C12M 25/00* (2013.01); *C12M 25/06* (2013.01); *C12M 41/46* (2013.01); *G01N 15/1463* (2013.01); *G01N 33/5014* (2013.01); *G01N 33/5061* (2013.01); *C12N 2503/02* (2013.01); *C12N 2535/10* (2013.01); *G01N 2015/0065* (2013.01); *G01N 2015/1006* (2013.01); *G01N 2015/1497* (2013.01)

(58) Field of Classification Search
None
See application file for complete search history.

(56) References Cited

U.S. PATENT DOCUMENTS

| | | |
|---|---|---|
| 2002/0164313 A1 | 11/2002 | Tremblay |
| 2005/0260202 A1 | 11/2005 | Bernstein et al. |
| 2006/0258003 A1 | 11/2006 | Pinset |
| 2008/0299086 A1 | 12/2008 | Kanzaki et al. |
| 2010/0260680 A1 | 10/2010 | Yasuda et al. |
| 2011/0189719 A1 | 8/2011 | Kuo et al. |
| 2011/0229962 A1 | 9/2011 | Mizutani et al. |

(Continued)

FOREIGN PATENT DOCUMENTS

| | | |
|---|---|---|
| EP | 1664266 B1 | 5/2007 |
| EP | 1882736 A1 | 1/2008 |

(Continued)

OTHER PUBLICATIONS

Eng. translation (MT). Kanzaki, N. et al. Method for preparing cultured myocyte having high metabolizing function. Japanese Patent Application Publication No. JP2006296282(A). Date of Publication: Nov. 2, 2006. specif. pp. 1, 4.*
Bajaj, P. et al. 2011. Patterning the differentiation of C2C12 skeletal myoblasts. Integrative Biology 3: 897-909. specif. pp. 897, 898, 899.*
Ruiz, S.A. et al. 2008. Emergence of patterned stem cell differentiation within multicellular structures. Stem Cells 26(11): 2921-2927. specif. pp. 2, 5, 11.*
Monge, C. et al. 2012. Engineering muscle tissues on microstructured polyelectrolyte multilayer films. Tissue Engineering: Part A 18 (15 &16): 1664-1676. specif. pp. 1664, 1670.*

(Continued)

*Primary Examiner* — Thomas J. Visone
*Assistant Examiner* — Sharon M. Papciak
(74) *Attorney, Agent, or Firm* — Saliwanchik, Lloyd & Eisenschenk

(57) ABSTRACT

A method and device for standardizing myoblast differentiation into myotubes, including a substrate (1) and at least one cell-adhesive pattern (2) for culturing myoblasts on the substrate. The pattern (2) has an elongated surface. A central region (2C) and two lateral regions (2L) extend from the central region in both directions along a longitudinal axis of the pattern. The ratio between the maximum width ($W_C$) of the central region (2C) and the maximum width ($W_L$) of the lateral regions (2L) is greater than or equal to 2. The ratio between the length (L) and the maximum width ($W_C$) of the pattern (2) is less than or equal to 4. The method includes providing a device as described above, depositing myoblasts on at least one cell-adhesive pattern of the device, culturing the myoblasts in a differentiation medium to promote cell differentiation into myotubes and constrain elongation of the myotubes.

14 Claims, 15 Drawing Sheets

(56) References Cited

U.S. PATENT DOCUMENTS

| | | | |
|---|---|---|---|
| 2012/0094323 A1* | 4/2012 | Dekker | C12N 5/0657 435/32 |
| 2014/0072599 A1 | 3/2014 | Kinooka et al. | |

FOREIGN PATENT DOCUMENTS

| | | | |
|---|---|---|---|
| EP | 2180042 A1 | 4/2010 | |
| JP | 2006-509516 | 3/2006 | |
| JP | 2006296282 A * | 11/2006 | C12M 35/02 |
| JP | 2011-122953 A | 6/2011 | |
| JP | 2013-032385 A | 2/2013 | |
| WO | 01/79421 A2 | 10/2001 | |
| WO | 2010/044417 A1 | 4/2010 | |
| WO | 2012/118099 A1 | 9/2012 | |

OTHER PUBLICATIONS

Rossi, S.G. et al. 2000. Local control of acetylcholinesterase gene expression in multinucleated skeletal muscle fibers: individual nuclei respond to signals from the overlying plasma membrane. Journal of Neuroscience 20(3): 919-928. specif. pp. 919, 924, 927.*

Azioune et al., "Robust Method for High-Throughput Surface Patterning of Deformable Substrates", Langmuir, vol. 27, No. 12, Jun. 21, 2011, pp. 7349-7352. (Listed in International Search Report dated Mar. 3, 2015).

Azioune et al., "Simple and rapid process for single cell micropatterning", Lab on a Chip, vol. 9, No. 11, Jan. 31, 2009, pp. 1640-1642. (Listed in International Search Report dated Mar. 3, 2015).

Cimetta et al., "Production of arrays of cardiac and skeletal muscle myofibers by micropatterning techniques on a soft substrate", Biomed Microdevices, vol. 11, 2009, pp. 389-400.

Serena et al., "Soft substrates drive optimal differentiation of human healthy and dystrophic myotubes", Integr. Biol., vol. 2, 2010, pp. 193-201.

"English Translation of Office Action," for Japanese Application No. 2016-541358 dated Oct. 23, 2018.

Yamamoto et al., "Myotube Formation on Micro-Patterned Glass: Intracellular Organization and Protein Distribution in C2C12 Skeletal Muscle Cells," Journal of Histochemistry & Cytochemistry, vol. 56, 2008, pp. 881-892.

Wang et al., "Wnt/beta-catenin signaling suppresses Rapsyn expression and inhibits acetylcholine receptor clustering at the neuromuscular junction," The Journal of Biological Chemistry, vol. 283, 2008, pp. 21668-21675.

Tseng et al., "A new micropafferning method of soft substrates reveals that different tumorigenic signals can promote or reduce cell contraction levels", Lab on Chip, vol. 7, 2011, pp. 2231-2240.

Strochlic et al., "Wnt4 participates in the formation of vertebrate neuromuscular junction", PLoS One, vol. 7, 2012, e29976, 12 pages.

Polio et al., "A micropatterning and image processing approach to simplify measurement of cellular traction forces," Acta Biomaterialia, vol. 8, 2012, pp. 82-88.

Pavlath, Grace K., "Spatial and functional restriction of regulatory molecules during mammalian myoblast fusion", Experimental Cell Research, Academic Press, US, vol. 316, No. 18, Nov. 30, 2010, pp. 3067-3072.

Junkin et al., "Cellular self-organization by autocatalytic alignment feedback", Journal of Cell Science, vol. 124, 2011, pp. 4213-4220.

International Search Report and Written Opinion received for PCT Patent Application No. PCT/EP2014/078129, dated Mar. 3, 2015, 14 pages.

International Preliminary Report on Patentability received for PCT Patent Application No. PCT/EP2014/078129, dated Jun. 30, 2016, 11 pages.

Engler et al., "Myotubes differentiate optimally on substrates with tissue-like stiffness: pathological implications for soft or stiff microenvironments," Journal of Cell Biology, vol. 166, No. 6, 2004, pp. 877-878.

Engler et al., "Embryonic cardiomyocytes beat best on a matrix with heart-like elasticity: scar-like rigidity inhibits beating," Journal of Cell Science, vol. 121, No. 22, 2008, pp. 3794-3802.

Azioune et al., "Simple and rapid process for single cell micropatterning", Lab on a Chip, vol. 9, No. 11, Jan. 31, 2009, pp. 1640-1642.

Abmayr et al., "Myoblast fusion: lessons from flies and mice", Development, vol. 139, 2012, pp. 641-656.

* cited by examiner

FIG. 1
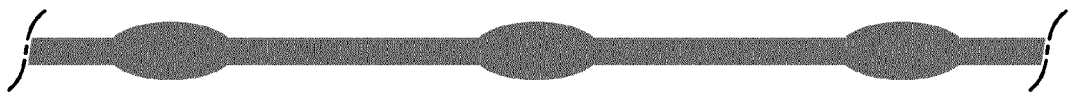
FIG. 2A
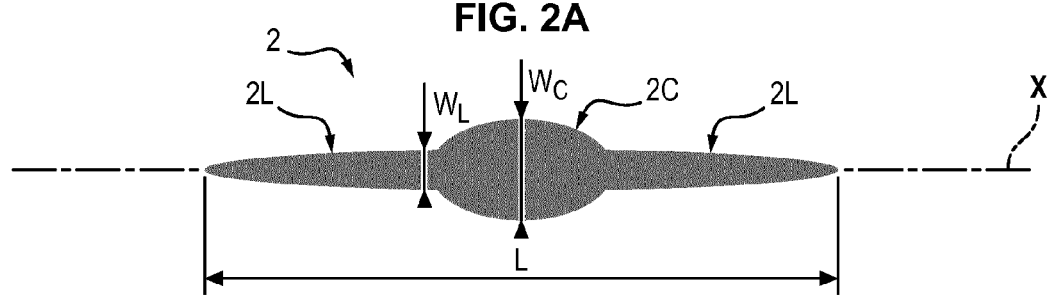
FIG. 2B
FIG. 2C
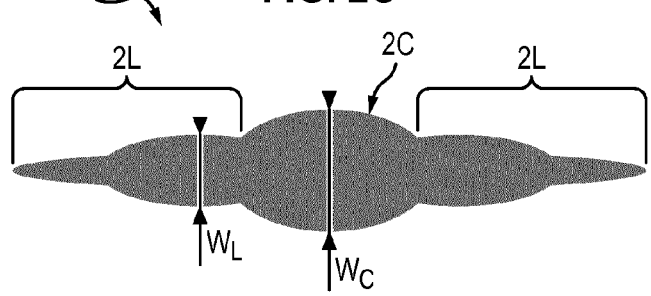
FIG. 2D
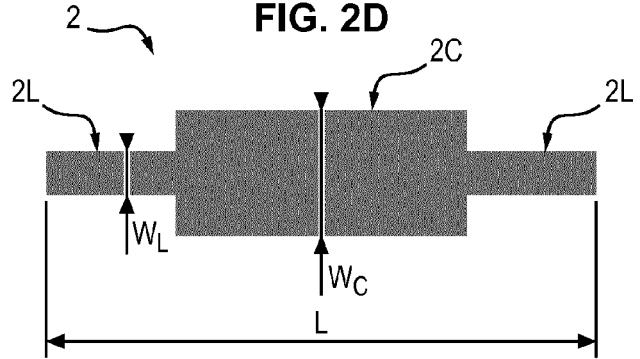

FIG. 5A
FIG. 5B
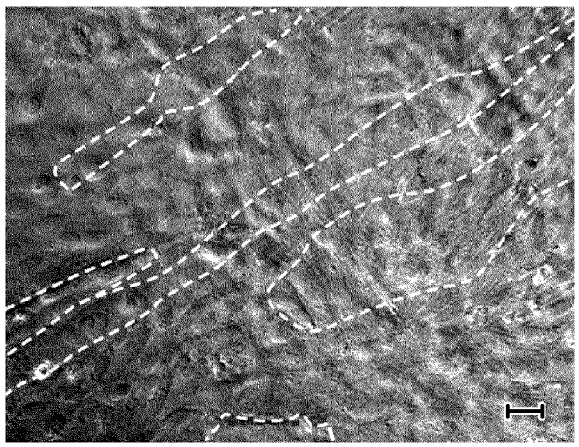
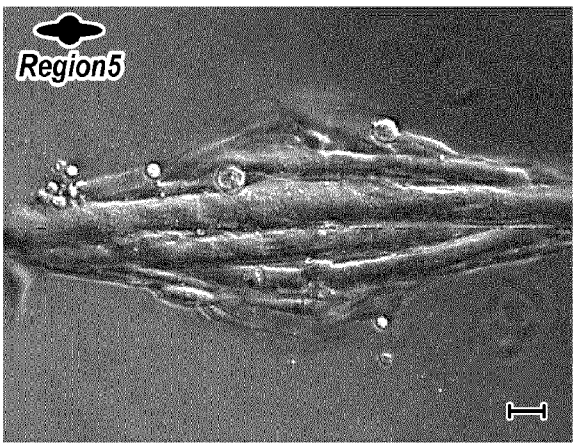

FIG. 9
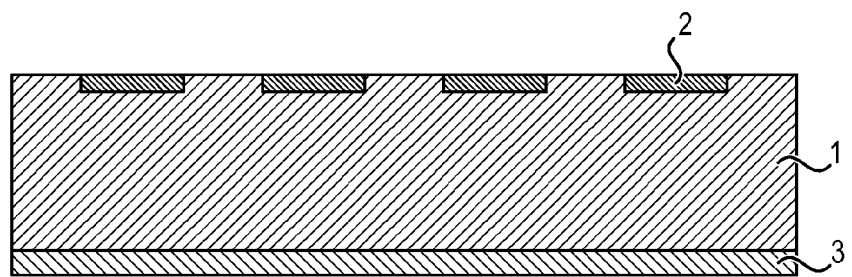
FIG. 10A
FIG. 10B
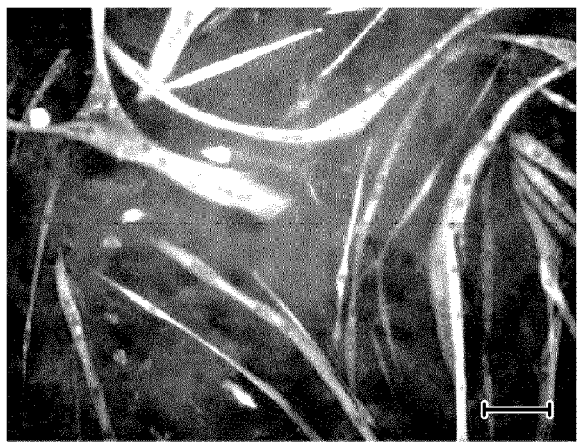
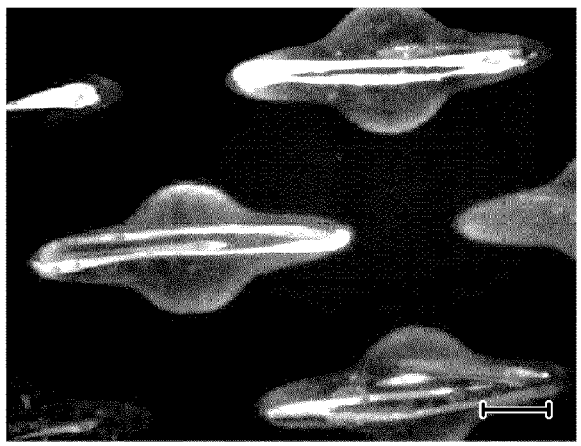

*** p<0,001, by student *t*-test, n=16

DEVICE AND METHOD FOR STANDARDIZING MYOBLAST DIFFERENTIATION INTO MYOTUBES

FIELD OF THE INVENTION

The invention relates to a device and a method for standardizing myoblast differentiation into myotubes, and a method for compound screening using such a device.

BACKGROUND OF THE INVENTION

Myogenesis is an in vivo process occurring during embryogenesis and tissue repair. Satellite cells begin to proliferate and form myoblasts. A myoblast is a mononucleate cell type that, by fusion with other myoblasts (this is a part of a process being also called "differentiation"), gives rise to myotubes that maturate and later eventually develop into muscle fibers. Maturation of myotubes can easily be characterized through the striated organization of myosin heavy chain molecules within sarcomeres, and the location of nuclei at the center of the structure [Abmayr 2012]. When myotubes are grown in a cell culture device, the growth method is intended to influence the growth of myotubes that are as close as possible as physiological myotubes.

Instead of substrates having a uniform, unpatterned cell-adhesive surface that generally provide a random orientation of the myotubes, patterned substrates have been demonstrated to enhance a specific orientation of myotubes.

Said patterns are typically in the form of lines, although finite geometrical shapes such as circular, square and Y-shaped patterns have also been investigated [Junkin 2011].

These experiments show that myotube morphological properties are strongly influenced by the shape of the pattern on which they are grown.

Other patterns consist of linear grooves formed in the surface of a substrate by an etching technique [Yamamoto 2008].

These lines are considered of an "infinite" length, meaning that their length is much greater than the length of the myotubes.

Some variations of these linear patterns have been tested in order to define the most appropriate shape with regard to myotube orientation.

In particular, so-called "hybrid" patterns that consist of the combination of a linear element and an arcuate element centered on the linear element, have proven to increase both the fusion index, i.e. the ratio of the number of nuclei in myocytes having two or more nuclei versus the total number of nuclei, and the maturation index, i.e. the number of myotubes having five or more nuclei; in addition, these pattern also provided a good alignment of the myotubes [Bajaj 2011]. More precisely, the pattern that provide the best results in this respect consists of a linear element having a width of 100 μm and a length of 2000 μm, whereas the arc degree of the arcuate element is of 30°. This so-called "hybrid" pattern is illustrated in FIG. 1.

Myoblast patterning on soft substrate (Young's modulus close to 10 to 15 kPa) have been shown to provide oriented myotubes with an increased maturity [Engler 2004].

However, although myotube orientation is extensively studied in the literature, their morphological parameters are poorly quantified and highly variable, due to difficulties in individualizing full mature structures and standardizing their morphology. This high variability level does not permit robust cell based assay development. Also, the level of achieved myotube maturation is still fare from in vivo like in term of striation and nuclei location.

SUMMARY OF THE INVENTION

A goal of the invention is to provide a device that allows standardization of myotubes morphological parameters such as their width and length, in view of carrying out cell-based assays.

According to a first aspect, the invention provides a device for standardizing myoblast differentiation into myotubes with highly reproducible morphological parameters.

Said device comprises a substrate and at least one cell-adhesive pattern for culturing myoblasts on said substrate, wherein:
  said pattern has an elongated surface comprising a central region and two lateral regions extending from said central region in both directions along a longitudinal axis of the pattern with a contour discontinuity between the central region and each lateral region, the length of the pattern being comprised between 100 and 1000 μm and the maximum width of said pattern being comprised between 50 and 500 μm,
  the ratio between the maximum width of the central region and the maximum width of the lateral regions is greater than or equal to 2,
  the ratio between the length and the maximum width of the pattern is less than or equal to 4.

According to an embodiment of the invention, the pattern is symmetrical according to its longitudinal axis and to a transversal axis perpendicular to the longitudinal axis.

According to an embodiment, the pattern consists of the partial superposition of three elliptical surfaces:
  a first elliptical surface defining the central region of the pattern and
  second and third elliptical surfaces having a major axis coinciding with the major axis of the first ellipse defining the lateral regions of the pattern,
wherein the second and third elliptical surfaces intersect the first elliptical surface along their transversal axis.

According to a preferred embodiment, the ratio between the length and the maximum width of the pattern is of 2.5.

Preferably, the area of said pattern is comprised between 5,000 and 500,000 μm$^2$.

According to an embodiment, the substrate is a hard substrate.

Alternatively, the substrate is a soft substrate, the Young's modulus of the substrate being preferably comprised between 5 and 15 kPa.

Another object of the invention is a method for standardizing myoblast differentiation into myotubes using the above-described device, comprising:
  (i) providing said device,
  (ii) depositing myoblasts on at least one cell-adhesive pattern of said device,
  (iii) culturing said myoblasts in a differentiation medium during a determined incubation time so as to promote cell differentiation into myotubes and constrain elongation of the myotubes on the cell-adhesive pattern.

Myoblast differentiation and the maturation of formed myotubes are found increased by using the invention, and become very close to the ones observed in vivo during the later phases of myogenesis up to the establishment of neuromuscular junction (NMJ).

Another aspect of the invention is its benefits for developing cell-based assays in particular but not limited to, related to myotoxicity and drug discovery. The standardization of myotubes morphology, coupled to the characterized benefits in term of myotube maturity, provides a reliable tool for the detection of subtle compounds effects on the physiology of myotubes differentiated from myoblasts taken on healthy and pathologic donors.

BRIEF DESCRIPTION OF THE DRAWINGS

Further features and advantages of the invention will be apparent from the following detailed description, referring to the appended drawings wherein:

FIG. 1 illustrates a "hybrid" pattern according to [Bajaj 2011] with an arc degree of 30°;

FIGS. 2A to 2D illustrate a cell-adhesive pattern according to different embodiments of the invention;

FIGS. 5A and 5B show respectively a phase contrast microscopy image of C2C12 myotubes grown on an unpatterned substrate and on a pattern according to the invention (in this case, the pattern of region 5 of FIG. 3);

FIG. 9 is a sectional view of a device according to the invention wherein the cell-adhesive pattern is formed on a soft substrate;

FIGS. 10A and 10B show respectively the shape of C2C12 myotubes on an unpatterned soft substrate and on a pattern according to the invention (in this case, the pattern of region 5 of FIG. 3);

DETAILED DESCRIPTION OF EMBODIMENTS OF THE INVENTION

Figure 3:
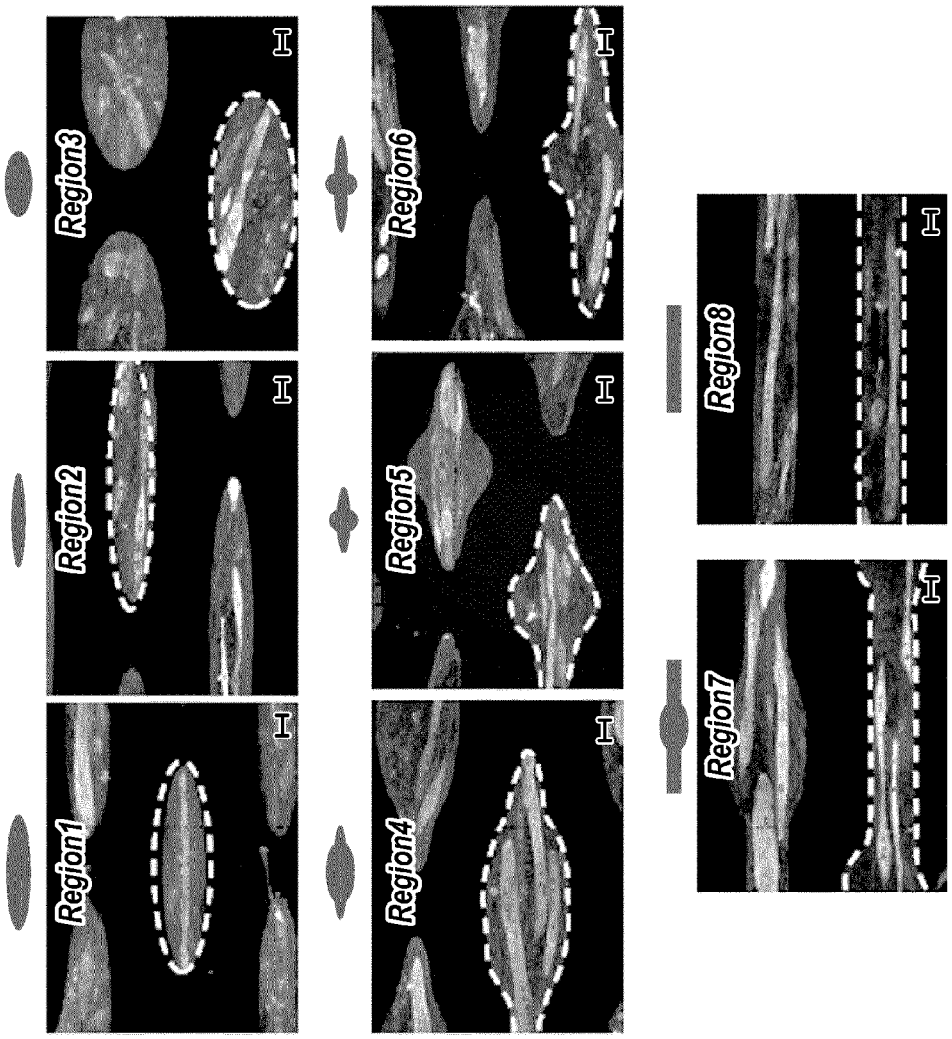
FIG. 3 illustrates the layout of a device wherein different cell-adhesive patterns have been formed (regions 1 to 8), said device also including an unpatterned region (region 9), and a picture of the C2C12 myotubes formed in each region.
Figure 3:
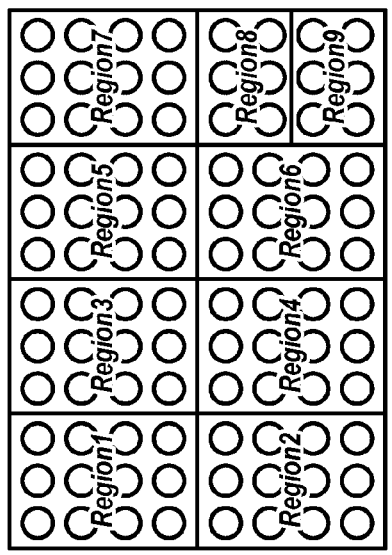
Figure 3:

According to the invention, the cell-adhesive pattern has an elongated surface with a specific shape.

More precisely, the pattern comprises, on the one hand, a central region and, on the other hand, two lateral regions extending from said central region in both directions along a longitudinal axis of the pattern.

By "elongated" is meant that the maximum dimension of the pattern can be measured along said longitudinal axis and is greater than the maximum dimension of the pattern along a transversal axis perpendicular to the longitudinal axis.

The dimension along the longitudinal axis is thus called "length" and the dimension along the transversal axis is called "width".

The lateral regions are generally narrower (along the transversal axis) than the central region.

In addition, there is a contour discontinuity between the central region and each lateral region. In other words, at the junction between the central region and a lateral region, the tangent to the contour of the central region does not coincide with the tangent to the contour of the lateral region.

For example, the pattern may be considered as a combination of at least three geometrical surfaces that are partially superimposed in the central region of the pattern.

Although not limited to this embodiment, the pattern is advantageously symmetrical with respect to both the longitudinal axis and the transversal axis.

According to an embodiment, each lateral region has a continuous contour.

Alternatively, at least one lateral region and/or the central region comprises itself a contour discontinuity.

In such an embodiment, the lateral region and/or central region may be considered as a combination of at least two geometrical surfaces that are partially superimposed.

When the lateral region is a combination of at least two geometrical surfaces, the maximum width of each surface decreases from the central region to the end of the pattern.

In a pattern according to the invention, the ratio between the maximum width of the central region and the maximum width of the lateral regions is greater than or equal to 2.

In addition, the ratio between the length and the maximum width of the pattern is less than or equal to 4.

As compared to a known "hybrid" pattern as illustrated in FIG. 1, a pattern according to the invention can be considered as having a "finite" length, meaning that the length of the pattern substantially corresponds to the length of the myotubes. To the contrary, the "hybrid" pattern has a substantially "infinite length", i.e. a length that is much greater than the length of the myotubes. For example, the length of the "hybrid" pattern is typically greater than several mm, e.g. greater than 6 mm.

Of course, this is a relative notion since the length of the pattern may be adjusted depending on the morphology required for resulting myotubes; this is why the dimensions of the pattern are not defined by numerical values but rather by ratios between different specific dimensions.

Typically, the length of the pattern may be comprised between 100 and 1000 μm, the width of the pattern may be comprised between 50 and 500 μm and the area of the pattern may be comprised between 5,000 and 500,000 μm².

Thanks to its shape and "finite" length, the pattern allows confining the myotubes and thus constraining them so as to spatially guide their initiation and elongation.

As will be shown in the experimental results below, such a pattern having a wider central region and narrower lateral regions has the following effect on myotubes differentiation: due to its width, the central region is a surface where the cells that are seeded thereon may migrate freely. To the contrary, the narrower lateral regions provide an increased constraint on the cells (said constraint preferably increasing toward the ends of the pattern) and thus guide them along a preferred direction, which is the longitudinal axis of the pattern. The myoblast fusion and myotube elongation is thus controlled along said preferred direction.

Besides, the pattern can be imaged in its entirety by conventional imaging methods and thereby allows measuring the length of the myotubes grown thereon. Hence, the pattern provides additional information regarding the myotubes.

To the contrary, an "infinite" pattern such as the "hybrid" pattern described above cannot be imaged as a whole due to its excessive length and thus does not allow measuring the length of the myotubes grown thereon.

FIGS. 2A to 2D illustrate various embodiments of a cell-adhesive pattern according to the invention.

In FIG. 2A, the central region 2C of the pattern has a substantially elliptical shape with a maximum width $W_C$.

Each lateral region 2L has the shape of a portion of ellipse with a maximum width $W_L$.

The main axes of the ellipses that define the central region and the lateral regions coincide.

The junction between each lateral region and the central region is located approximately at the transversal axis of the ellipse defining the lateral region.

The length of the pattern is referred to as L.

In FIG. 2B, the central region 2C has substantially the shape of two joint ellipses. The maximum width $W_C$ of the central region is the maximum dimension of both ellipses along their transversal axis.

As in FIG. 2A, each region 2L has the shape of a portion of ellipse with a maximum width $W_L$.

The junction between each lateral region and the central region is located approximately at the transversal axis of the ellipse that defines the lateral region.

In FIG. 2C, the central region 2C has substantially the shape of an ellipse, as in FIG. 2A.

Each lateral region 2L has the shape of two joint ellipses, wherein the ellipse closest to the central region has a greater width than the ellipse farthest from the central region.

In such case, the maximum width of each lateral region 2L is defined as being the maximum width of the wider ellipse.

The shape of the pattern may not be rounded as shown in FIGS. 2A to 2C.

For example, as shown in FIG. 2D, the central region 2C of the pattern has a rectangular shape having a width $W_C$ and each lateral region 2L has a rectangular shape having a width $W_L$.

Of course, the embodiments illustrated in FIGS. 2A to 2D are only examples and are not intended to limit the scope of the invention. Any other pattern complying with the above-described dimensional requirements is part of the invention.

Such a pattern is formed on a substrate so as to form a device for culturing and maturing myoblasts. While the pattern surface is cell-adhesive, the surrounding surface of the substrate is not cell-adhesive, or less cell-adhesive, so as to hinder myotube growth outside of the pattern.

According to an embodiment, the substrate is a hard substrate typically used for culturing cells, such as glass, silicone, plastics (e.g. polystyrene, polypropylene, polyethylene). By "hard" is meant here that Young's modulus of the substrate is greater than or equal to 1 MPa. According to another embodiment, the substrate is a soft substrate. By "soft" is meant here that Young's modulus of the substrate is comprised between 5 and 15 kPa.

A Young's modulus around 10 kPa is considered to be the most appropriate for optimal differentiation and maturation [Engler 2008].

Such soft substrates include:
 synthetic hydrogels materials, such as poly(hydroxyethyl methacrylate) (PolyHEMA), polyacrylamide (PAA); polyethylene glycol (PEG), polyacrylic acid, Poly(vinyl alcohol) (PVA), polyvinylpyrrolidone, polyimide, polyurethane, etc. and the hybrids of above mentioned materials and their derivatives;
 natural hydrogel materials, such as agarose, dextran, gelatin, matrigel, DNA, polyisocyanopeptides, etc.;
 silicone materials.

Such soft materials are already used for culturing cells. The patterns can be formed on such substrates by known techniques including:
 microcontact printing [Engler 2004],
 deep UV activation [Tseng 2011],
 micropatterns transfer [Polio 2012],
 photochemical binding [Hahn 2006].

Patterns in the form of lines or grooves on soft substrates have been reported in the literature [Serena 2010], [Cimetta 2009], [Monge 2012], US 2011/0189719.

The standardization of myoblast differentiation into myotubes typically comprises the following steps.

First, a device for culturing said myoblasts and comprising a substrate (either soft or hard) and at least one cell-adhesive pattern as described above formed on said substrate is provided.

Then, myoblasts are deposited on at least one cell-adhesive pattern.

The myoblasts are incubated in a growth medium during a given growth time.

After this growth step, the cells are cultured in a differentiation medium during a determined incubation time so as to promote cell differentiation into myotubes and constrain elongation of the myotubes on the cell-adhesive pattern.

For example, for C2C12 mouse cells, the growth medium is DMEM, 20% FBS, 0.5% P/S and the growth time is 24 hours; the differentiation medium is DMEM/F12, 2% Horse Serum, 0.5% P/S and the incubation time is from 7 to 11 days, the differentiation medium being changed every 2 days. (In the present text, the % used to define a composition refers conventionally to a weight in grams per 100 ml.)

At the end of this incubation time, the cells may be stained to reveal differentiated myotubes.

However, as will be shown below, the pattern according to the invention improves the aspect of myotubes and allows detecting myotubes by phase contrast microscopy without immunostaining.

Hard Substrate

FIG. 3 illustrates the layout of a device wherein different cell-adhesive patterns have been formed (regions 1 to 8), said device also including an unpatterned region (region 9), and a picture of the myotubes formed in each region.

In regions 1, 2 and 3, the patterns have an elliptical shape with different length/width ratios: such patterns are not within the scope of the present invention.

Regions 4, 5 and 6 comprise patterns according to embodiments of the invention. In each case, the central region of the pattern is elliptical and the lateral regions are portions of an ellipse. These patterns differ by the length/width ratio of the central region and lateral regions.

In region 7, the pattern is a "hybrid" pattern as illustrated in FIG. 1. As already mentioned, such a pattern is not within the scope of the present invention.

In region 8, the pattern is a line, which is not within the scope of the present invention.

Table 1 shows the respective micropattern dimensions from each region.

TABLE 1

|  | Width Wc (µm) | Length L (µm) | Area (µm²) |
| --- | --- | --- | --- |
| Region 1 | 100 | 500 | 39220 |
| Region 2 | 100 | 750 | 58831 |
| Region 3 | 200 | 500 | 78444 |
| Region 4 | 200 | 750 | 92301 |
| Region 5 | 200 | 500 | 52200 |
| Region 6 | 200 | 750 | 71686 |
| Region 7 | 200 | 8800 | 1760000 |
| Region 8 | 100 | 26300 | 2617400 |

On each picture, the pattern is delineated by a dotted line.

C2C12 mouse or primary human myoblasts (HSMM, Lonza) were cultured on fibronectin coated micropatterns within growth medium (DMEM, 20% FBS, 0.5% P/S, or Lonza SkGM™-2 cell culture Kit respectively) during 24 hours. Then both cell types were cultured within differentiation medium (DMEM/F12, 2% Horse Serum, 0.5% P/S) during 5 to 11 days for HSMM and C2C12 respectively. Differentiation medium were changed every 2 days. Cells were fixed and an immunostaining was realized against myosin heavy chain (in green in a color image—in light grey in the appended black&white figures), actin (in red in a color image—in medium grey in the appended black&white figures) and nuclei (in blue in a color image—in dark grey in the appended black&white figures). Images were acquired using an epifluorescence microscope (DMI6000, Leica).

FIGS. 4A to 4D show respectively the fusion index (ratio of nuclei within myotubes of the total number on nuclei), the maturation index (number of nuclei per myotubes), the orientation angle and the width/length ratio of the myotubes for each type of pattern shown in FIG. 3.

However, the angular orientation of the myotubes on the patterns is well reproducible (angle near to 0 whatever the shape of the pattern), as compared to an unpatterned substrate, on which the myotubes may take any orientation.

Figure 4A:
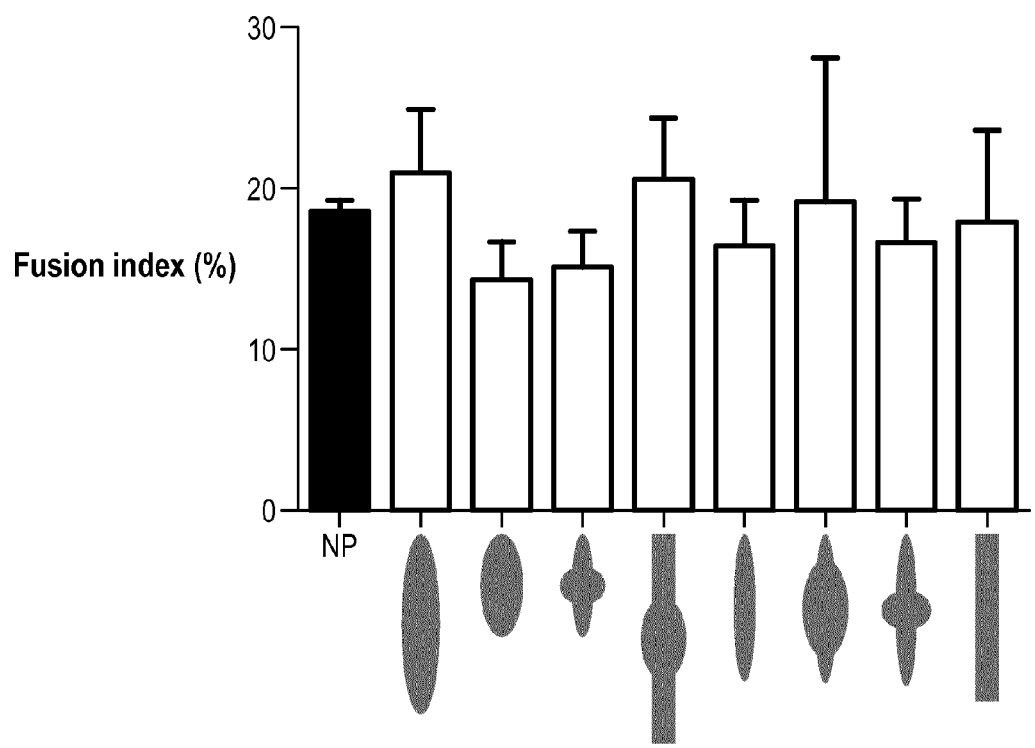
FIGS. 4A to 4D show respectively the fusion index, the maturation index, the orientation angle and the width/length ratio of the C2C12 myotubes for each type of pattern shown in FIG. 3.
Figure 4B:
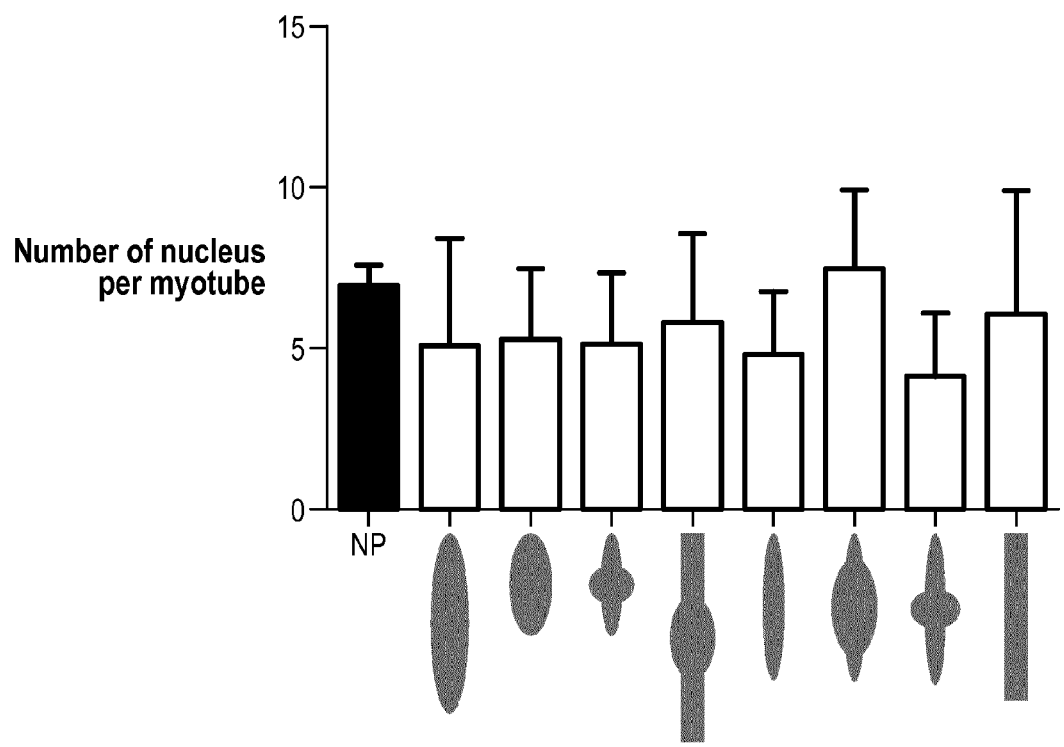
Figure 4C:
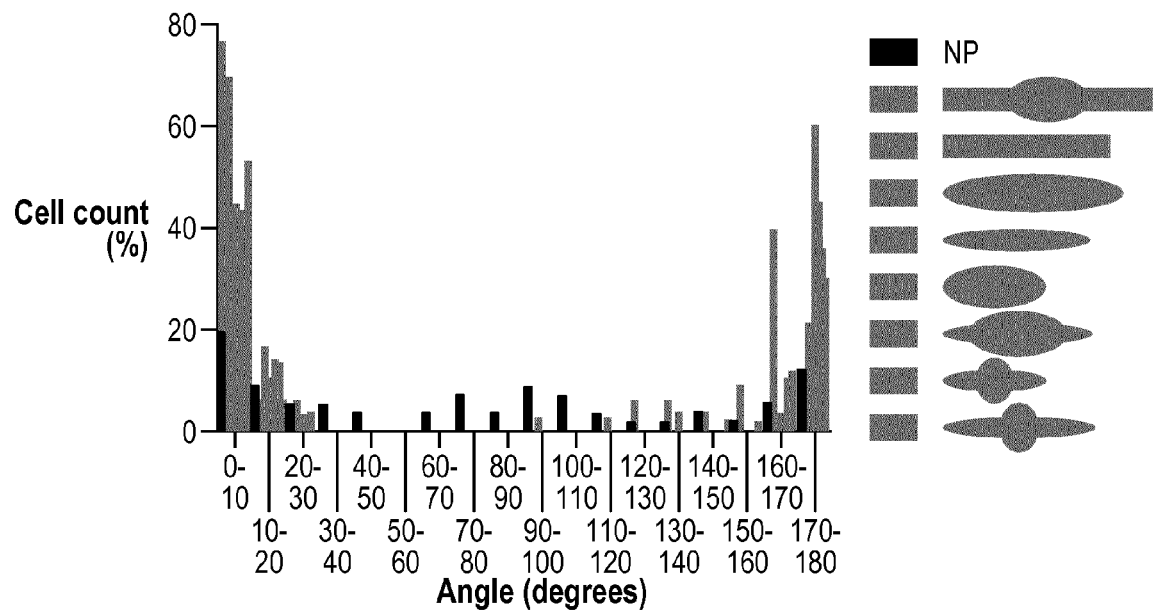
Figure 4D:
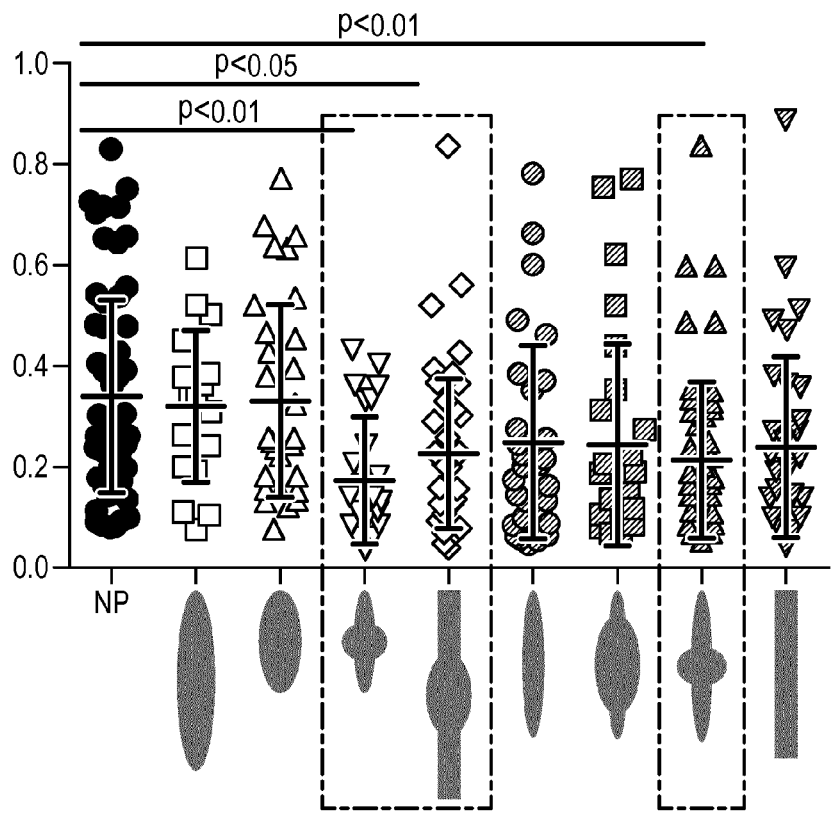

At last, FIG. 4D shows that the width/length ratio of the myotubes is more stable (i.e. its variability is reduced) with the known "hybrid" pattern and with some embodiments of the pattern according to the invention. In other words, said specific patterns allow standardizing myotube shape as compared to an unpatterned substrate. Moreover region 5 micropattern shows the lower width/length ratio compared to the other tested patterns, indicating that myotubes are more elongated and subsequently more mature compared to "myosacs"-like structures, which are known to be rounded (with higher width/length ratio) and formed during the first steps of in vitro differentiation. In other words, this design provides an increased myotube maturity.

Depending on the type of myoblasts, lateral regions having a small length such as in region 4 may not be sufficient to constrain the cells. The length of the lateral regions of the pattern may thus be adjusted depending on the type of cells to be grown thereon.

FIGS. 5A and 5B show respectively a phase contrast microscopy image of myotubes grown on an unpatterned substrate and on a pattern according to the invention (in this case, the pattern of region 5 of FIG. 3). In both cases, the cells have not been stained and images were acquired using phase contrast microscopy.

These images show that the visual aspect of the myotubes is significantly improved by the pattern according to the invention, even without cell staining. This can be explained by the fact that the constraint exerted by said pattern generates a more pronounced relief of the myotubes, which is easily observable using a phase contrast device.

Besides, these images of FIG. 3 show that on an unpatterned substrate (region 9), the myotubes exhibit artifactual branching (which does not occur in physiological myotubes), whereas on a pattern according to the invention (in particular region 5), the myotubes are linear and do not exhibit such branching. In other words, the pattern provides a more physiological myotube differentiation.

Figure 6:
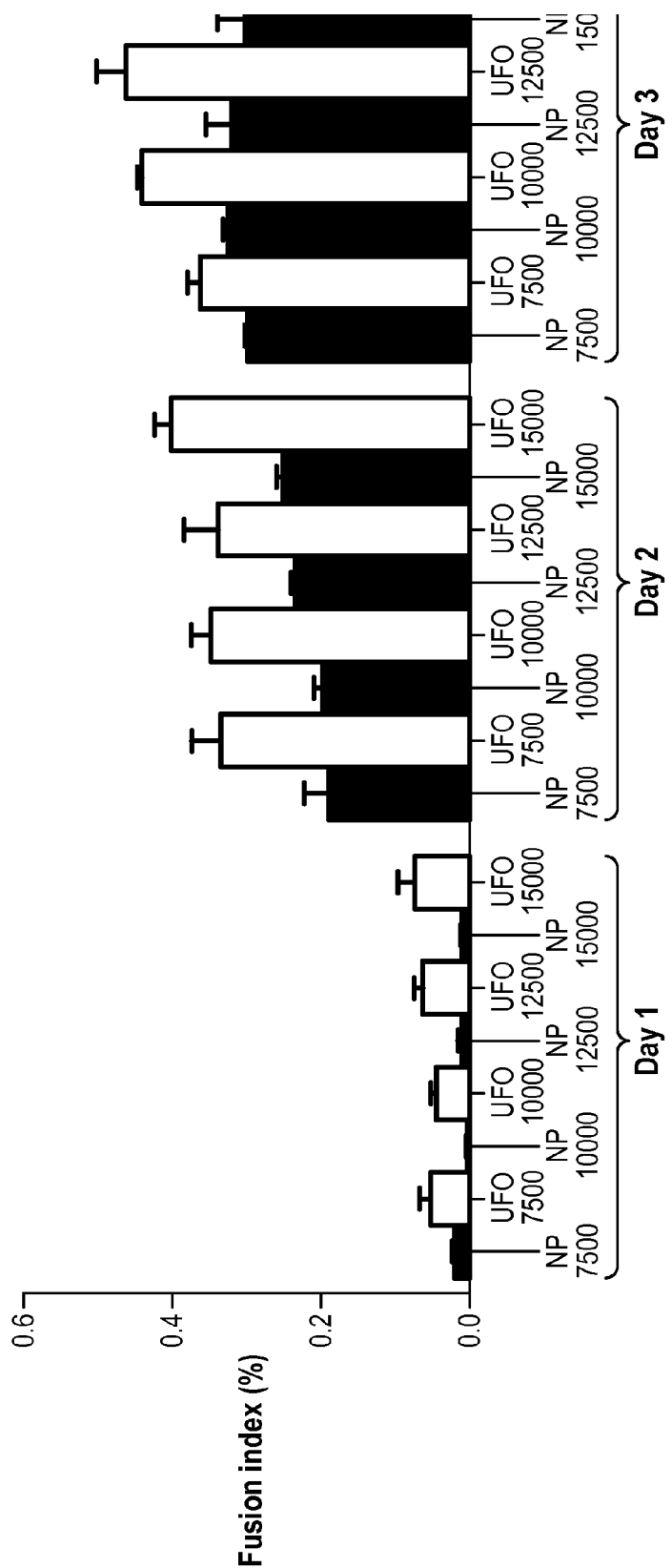
FIG. 6 is a time course, with different primary human myoblasts cell densities, showing an increase of the fusion index on micropatterns according to the invention (in this case, the pattern of region 5 of FIG. 3) compared to unpattern surfaces, for a fixed time point.

FIG. 6 shows the evolution of the fusion index over the first 3 days of differentiation, for different cell densities. These quantifications demonstrate that cell differentiation is increased with cell density and more importantly that micropatterns (in this case, the pattern of region 5 of FIG. 3) accelerate myoblast differentiation.

Figure 7B:
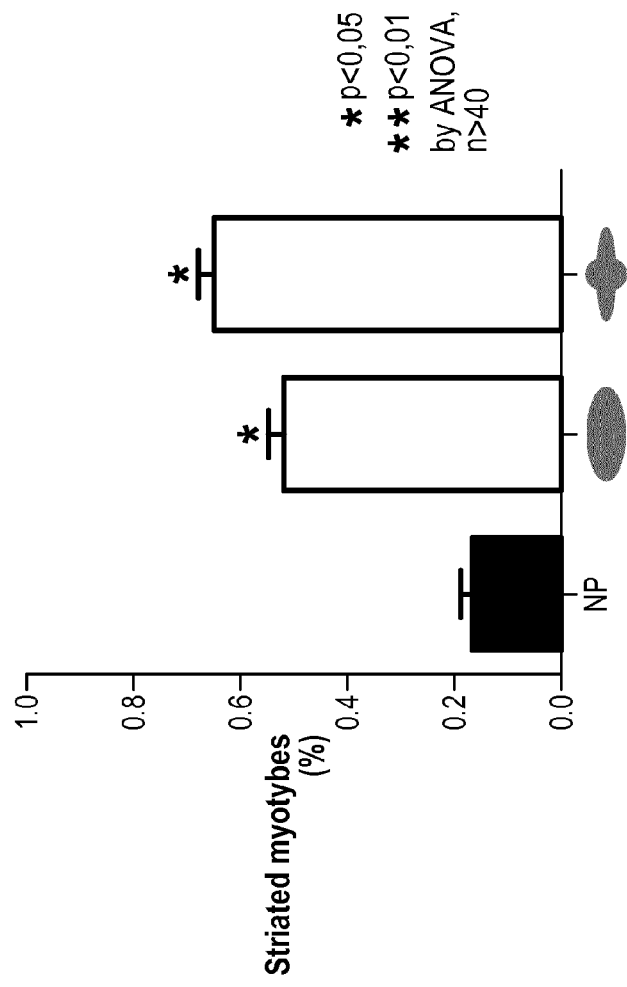
FIG. 7B is a quantification of striated myotubes after 3 days of differentiation on said micropatterns and unpatterned surfaces.
Figure 7A:
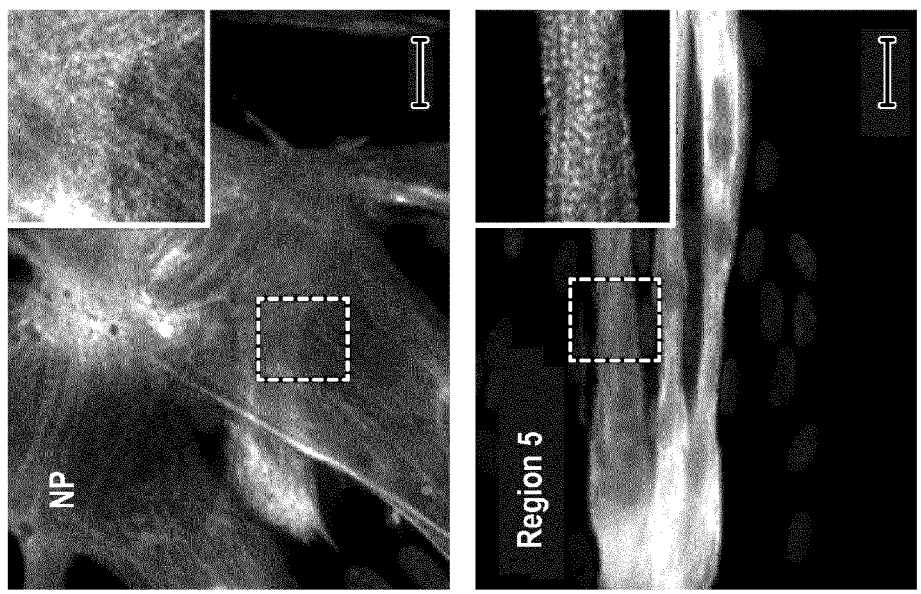
FIG. 7A shows striation of myotubes from primary human myoblasts on unpatterned (top) and micropatterned (according to the invention using the pattern of region 5 of FIG. 3, bottom) surfaces. Representative levels of myotube maturity (through sarcomera striation) are shown on enlargements on the top right of the pictures.

FIGS. 7A and 7B illustrate and quantify the improvement of sarcomera striation, a maturation marker of myotubes, within structures cultured on micropatterned (region 5 of FIG. 3) compared to unpatterned substrates.

Figure 8A:
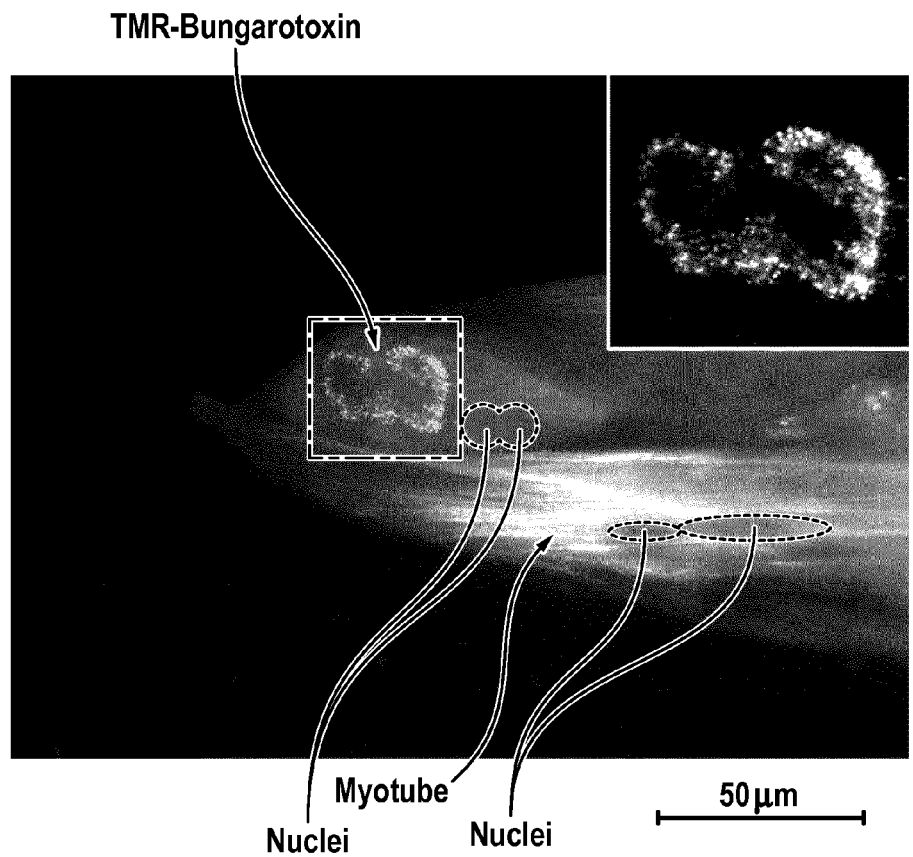
FIG. 8A shows primary human myotube cultured on micropatterns with acetylcholine receptor clustering forming an in vivo-like structure, known as "pretzel", due to agrin treatment.
Figure 8B:
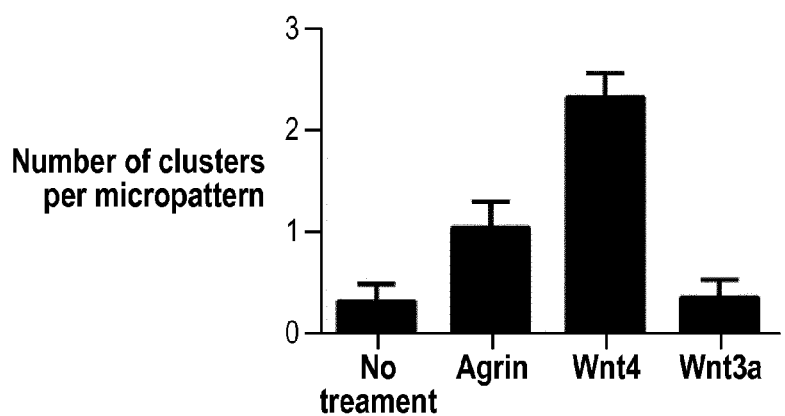
FIG. 8B is a quantification of the regulation of cluster formation through agrin and Wnt signaling.

FIG. 8A shows the ability of myotubes cultured on micropatterns to recapitulate the first step of neuromuscular junction formation. Following agrin treatment, micropatterned myotubes exhibit a large clustering of their acetylcholine receptors (AChR). Here, TMR-Bungarotoxin was used as a florescent probe to interact with the acetylcholine receptors, subsequently revealing their location. Moreover, at their lateral extremities, AChR clusters were found to have perforations resulting in pretzel-like structures with synaptic nuclei recruitment, recapitulating classical traits of post-synaptic maturation of NMJ in vivo. Moreover, FIG. 8B shows that Wnt3a and Wnt4 molecules treatment, respectively known to inhibit and stimulate AChR clustering in mice [Strochlic 2012, Wang 2008], fully recapitulate the in vivo situation with myotubes derived from human primary cells cultured on the present device.

Altogether these results show that micropatterns improve myotubes maturation. In conclusion, a pattern according to the invention reduces the variability of myotubes length and width, allows myotubes detection without immunostaining, facilitates identification and numeration of myotubes, provides an easier image analysis and quantification and improves overall myotube orientation and maturation including the capacity to recapitulate the first step of NMJ formation.

Soft Substrate

Myotube standardization can be further improved by incubating the cells on a pattern according to the invention formed on a soft substrate, as compared to the same pattern formed on a hard substrate.

As shown on FIG. 9, the device thus comprises a soft substrate 1 such as a hydrogel that is supported by a stiffener 3, such as a glass plate. A plurality of cell-adhesive patterns are formed on said soft substrate 2.

Patterns similar to the patterns of FIG. 3 have been formed on a soft substrate.

The protocol for cell incubation was the following.

C2C12 cells (murin myoblasts) were seeded on patterned hydrogels having a Young's modulus of 10 kPa.

The seeding conditions were: 300.000 cells/well in 3 ml culture medium.

A first incubation step was carried out during 24 hours, at 37° C., under 5% CO2, in a growth medium (DMEM (Gibco), 20% FBS (PAA), 0.5% P/S (Invitrogen)).

A second incubation step was carried out during 5 days at 37° C., under 5% CO2, in a differentiation medium (DMEM/F12 (1:1, Gibco), 2% horse serum (PAA), 0.5% P/S (Invitrogen). The medium was changed every 2 days.

Then, nuclei, actin and myosin were immunostained.

FIGS. 10A and 10B show respectively the shape of myotubes on an unpatterned soft substrate and on a pattern according to the invention (in this case, the pattern of region 5 of FIG. 3).

As already observed for an unpatterned hard substrate, myotubes exhibit artefactual branching, which is not representative of physiological myotubes.

By contrast, the myotubes incubated on a pattern formed on a soft substrate exhibit a linear shape, which corresponds to a more physiological configuration.

Figure 11:
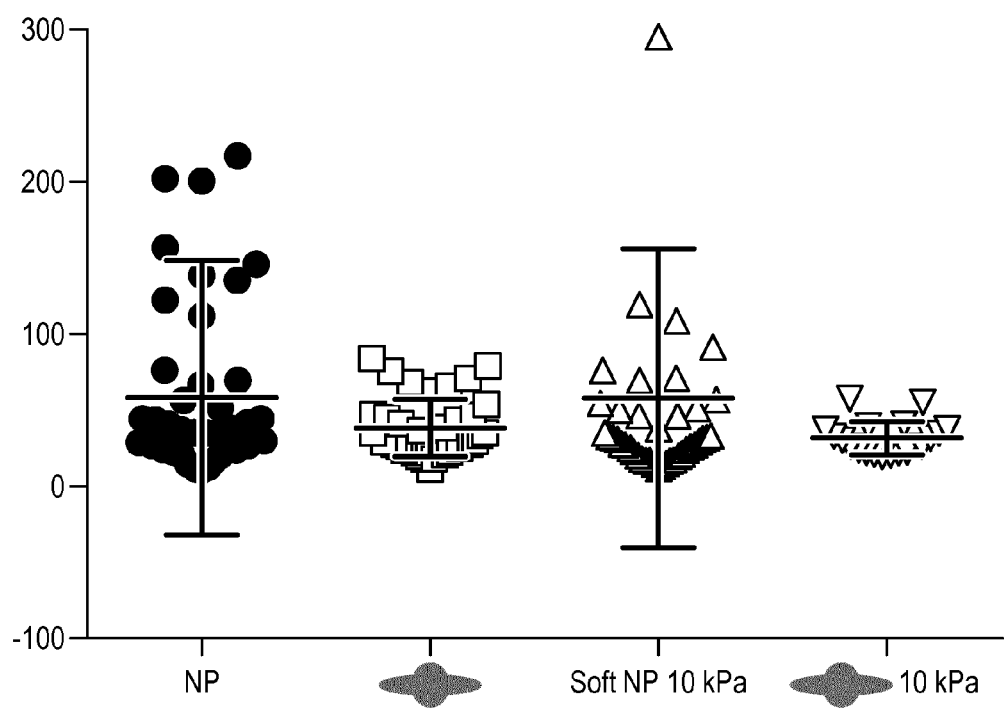
FIG. 11 shows comparisons of the width of C2C12 myotubes formed on devices encompassing or not micropatterns and/or soft substrates.

Myotubes are finer and present nuclei alignments which is typical of mature structures compared to hard substrates on FIG. 3. Moreover, morphological parameters of myotubes appear highly standardized between structures, even compared to hard substrate, as shown on FIG. 11.

Figure 12:
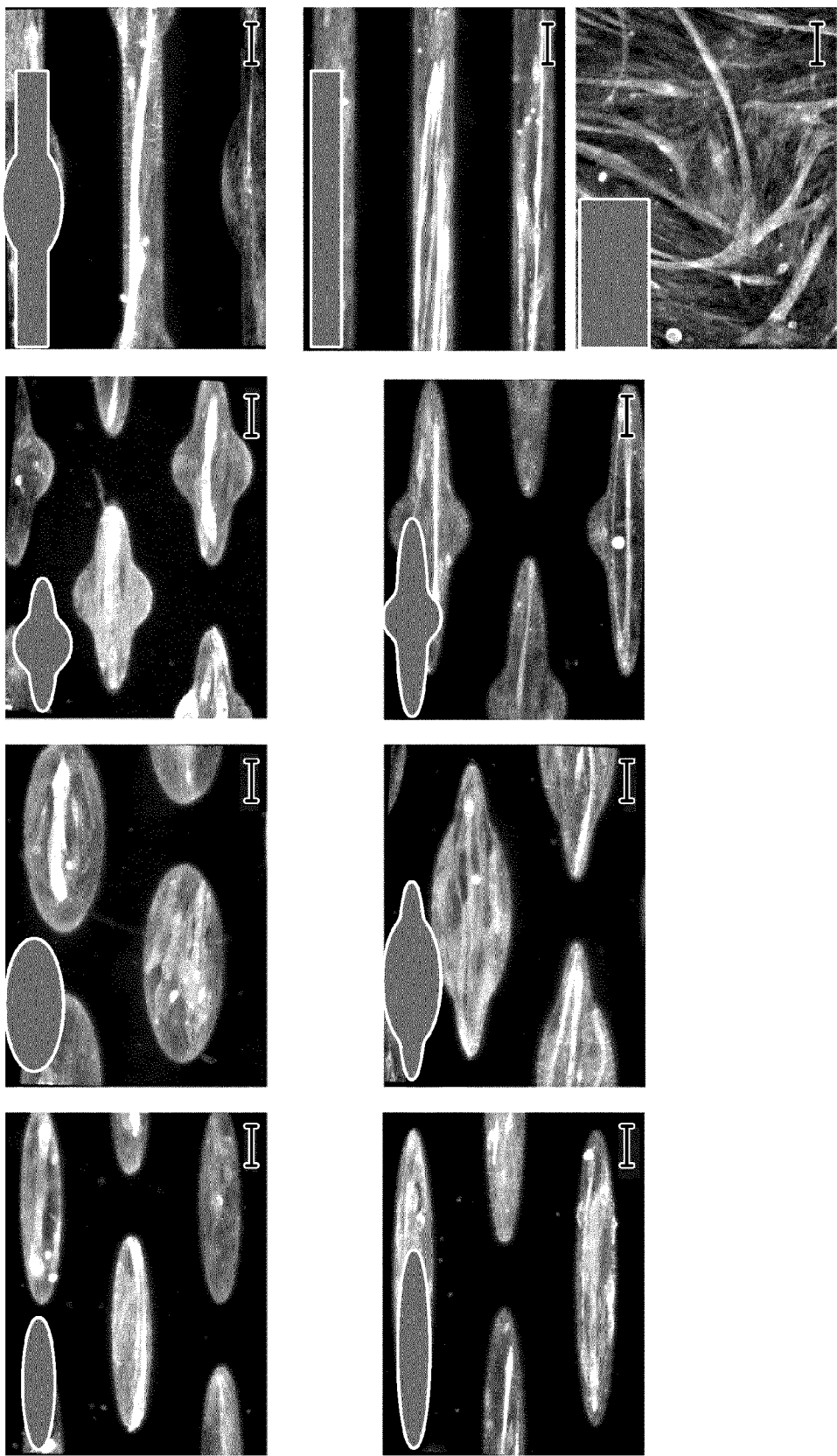
FIG. 12 shows the formation of C2C12 myotubes on a device comprising a soft substrate on which patterns having different shapes have been formed.
Figure 13A:
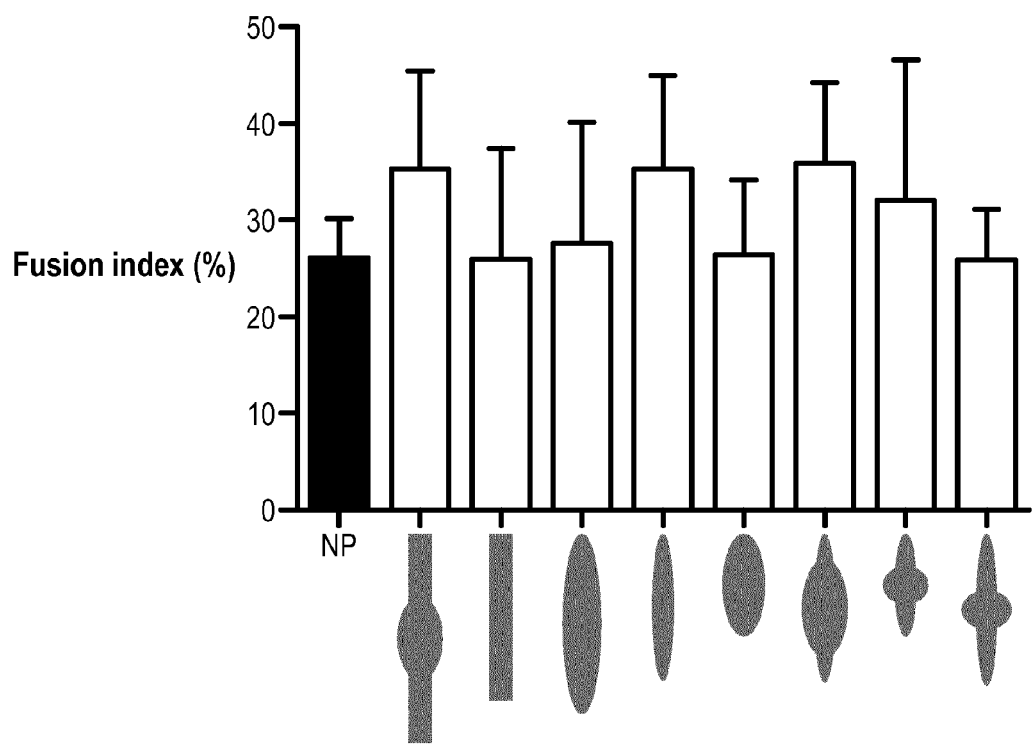
FIGS. 13A to 13F show respectively the fusion index, the maturation index, the orientation angle, the width/length ratio, the width and the length of the C2C12 myotubes for different patterns on a device comprising a soft substrate.
Figure 13B:
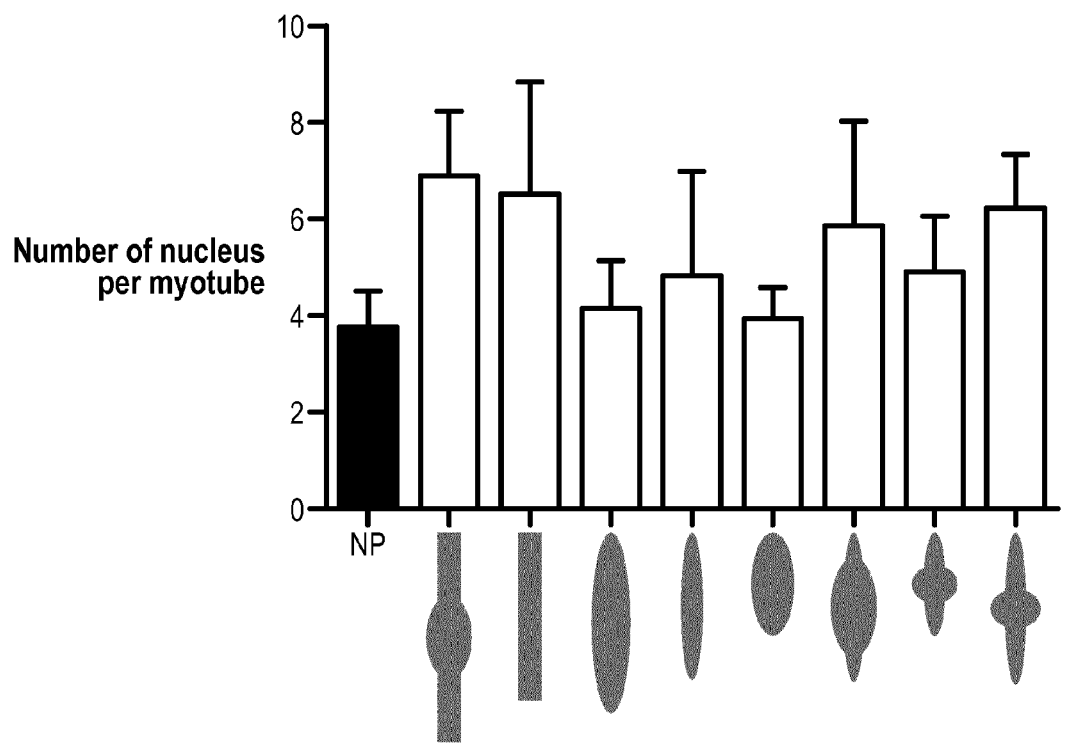
Figure 13C:
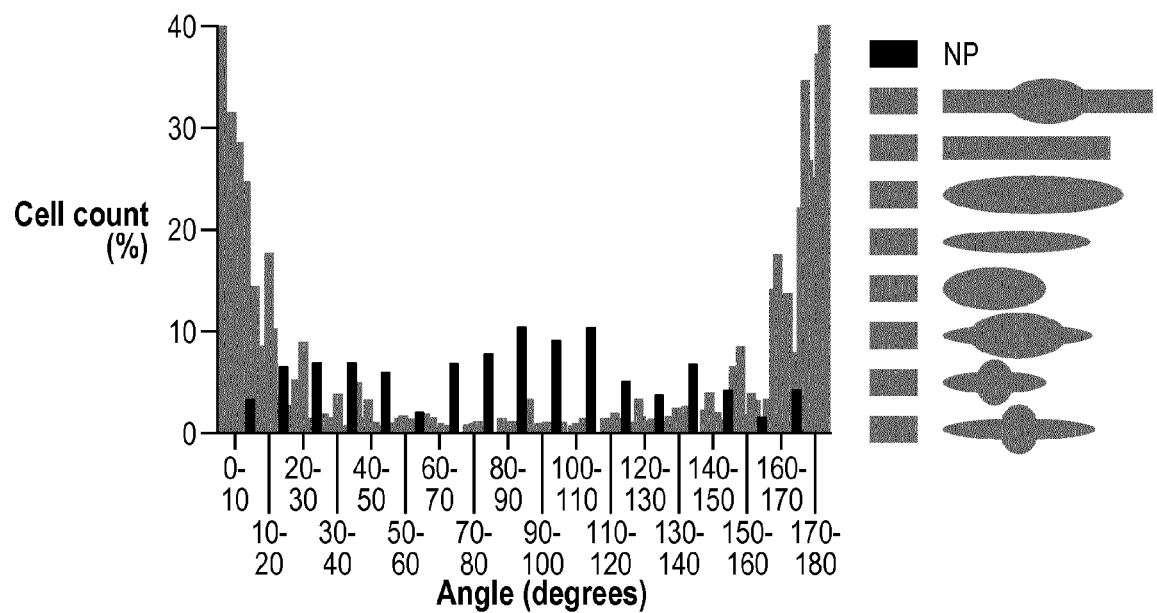
Figure 13D:
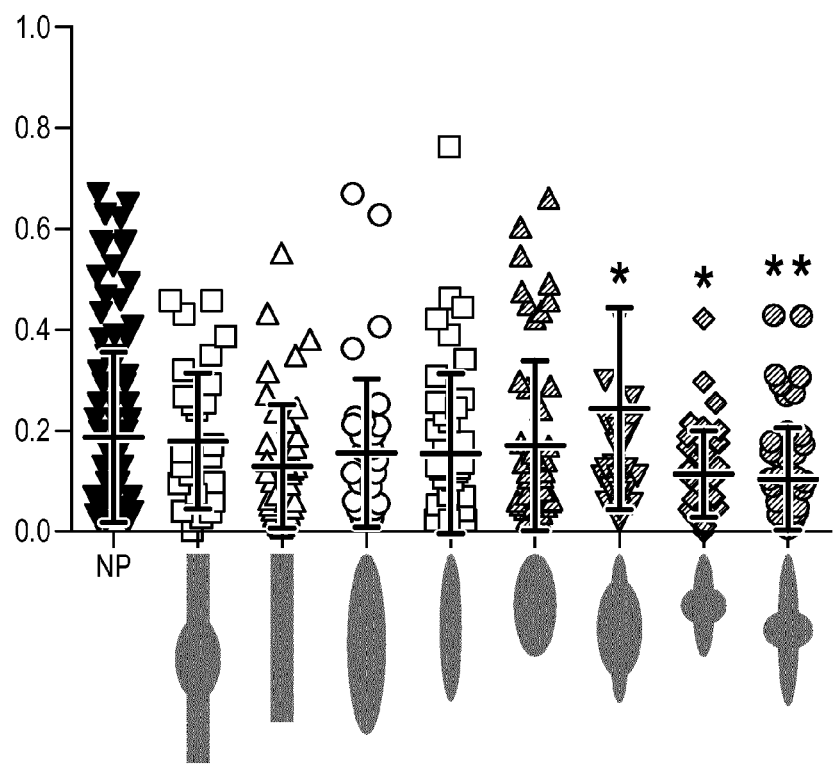
Figure 13E:
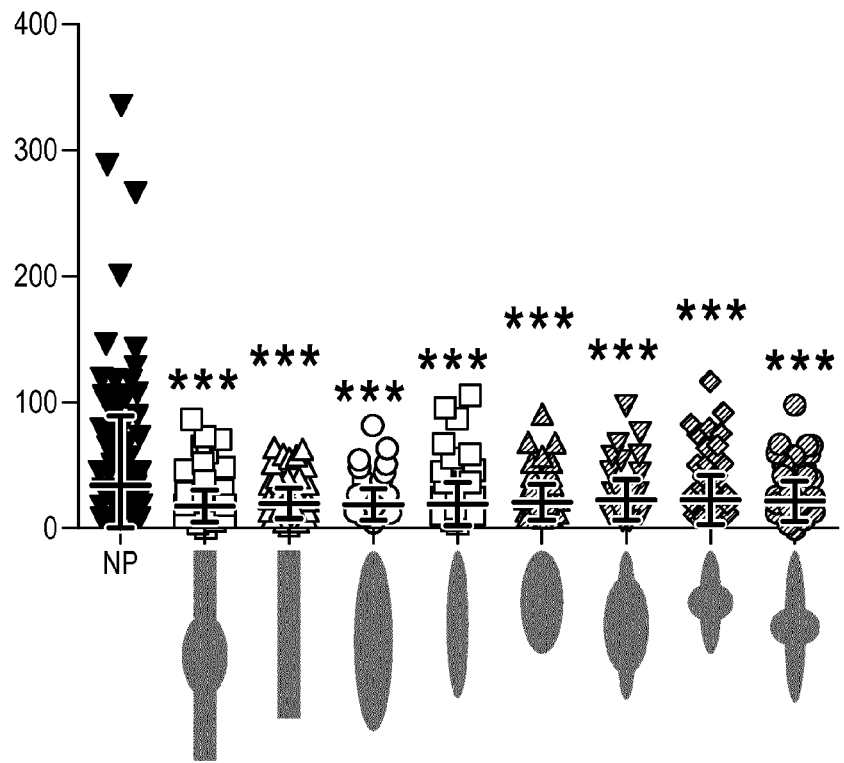
Figure 13F:
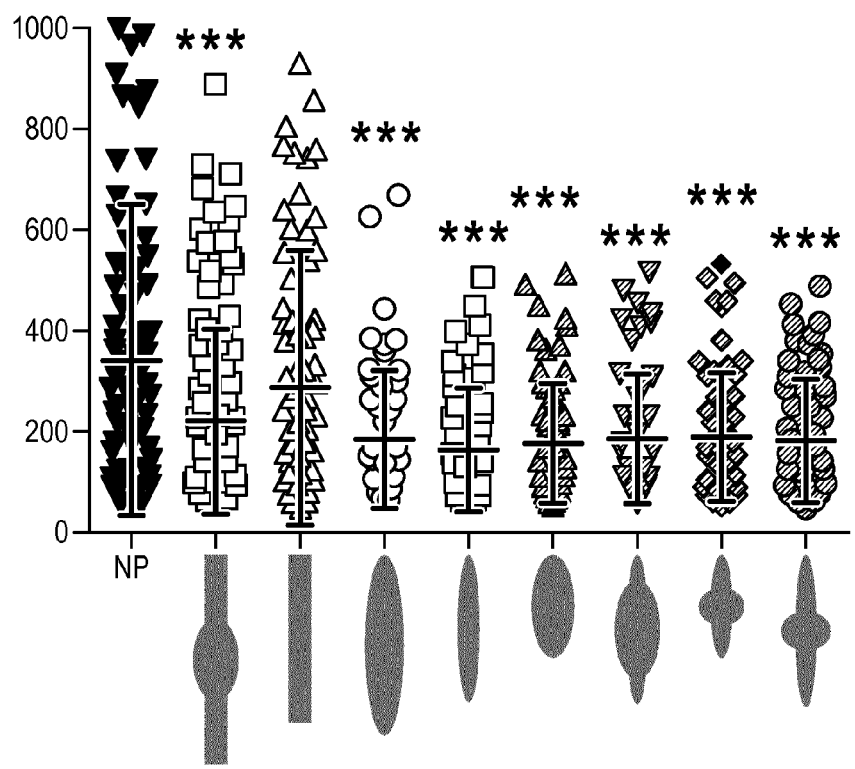

FIG. 12 shows the formation of myotubes on a device comprising a soft substrate on which patterns having different shapes have been formed.

Myotube formation is visible with all pattern geometries after 5 days in differentiation medium and is two times faster compared to hard substrate, indicating a strong effect on myoblast differentiation process.

FIGS. 13A to 13F show respectively the fusion index, the maturation index, the orientation angle, the width/length ratio, the width and the length of the myotubes for different patterns on a device comprising a soft substrate.

As with the hard substrate, all patterns provide substantially similar effects in terms of fusion index and maturation index.

In addition, the angular orientation of the myotubes incubated on patterns is reproducible as compared to a culture on an unpatterned substrate.

More significantly, the patterns according to the invention provide a reduced variability of the length and width of the myotubes, as compared to finite shapes such as ellipses and also to "infinite" shapes such as "hybrid" patterns and lines. See in particular the results obtained with the second pattern from the right on FIG. 13D, which are the best ones among the tested patterns.

The fact that myotubes are obtained with standardized length and width facilitates cell-based assays.

The pattern shape may be adjusted depending on the goal of the assay and on the desired width and length of the myotubes.

Cell Based Assays

One advantage of the invention is its compatibility with high content screening cell based assays, which allows various applications such as testing myotoxicity and/or active compounds screening.

In particular, the invention provides a method for screening compounds driving changes in skeletal muscle cells and in particular myotubes or myoblasts.

The invention also provides a method for identifying compounds regulating skeletal muscle differenciation, maturation, atrophy and hypertrophy.

The invention also provides a method for studying molecular mechanisms regulating changes in skeletal muscle cells and in particular myotubes or myoblasts.

Micropatterns according to the invention, in particular patterns according to region 5 of FIG. 3 can be used in myotoxicity assays to characterize compounds mode of action on forming myotubes.

By myotoxicity is meant in the present text the effect of a compound on myoblasts differentiation, myotube maturation, myotube hypertrophy, myotube atrophy, or cell viability.

Another possible application of the invention is drug discovery.

In this regard, the invention provides a method for identifying therapeutic compounds acting on atrophy or hypertrophy of skeletal muscle cells and in particular myotubes or myoblasts.

By using myoblasts taken from donors having a muscle related disease and weakness (including myopathies, sarcopenia, cachexia, rhabdomyolysis, lysosomal myopathies, myofibrillar myopathies, inflammatory myopathies, hypakalemia myopathies, corticosteroid myopathies, myosin deficiency, myastenia, myositis, and muscle defects due to neuron disorders) from a cell line, isogenic cell line, stem cells derived (including IPs, ES), compounds can be screened to find candidates that may allow discovering new drugs having curative effects on the targeted pathology: for example compounds providing hypertrophy on myoblasts taken from patient suffering from rhabdomyolysis.

The screening method typically comprises the following steps. Such a screening method is carried out in vitro.

A device comprising cell-adhesive patterns as described above is provided.

According to a preferred embodiment, the patterns are the patterns of Region 5 in FIG. 3.

Myoblasts are deposited on the cell-adhesive patterns.

Depending on the goal of the cell based assay, the myoblasts may be obtained from a healthy donor (e.g. in view of testing compound toxicity) or from a donor suffering from a determined muscle related pathology (e.g. in view of testing curative effect of a compound on such myopathy) from a cell line, an isogenic cell line, derived stem cells (including IPs, ES). Obtaining the myoblasts is a preliminary step that is not included in the present invention.

The myoblasts are cultured in a differentiation medium so as to promote their differentiation into myotubes.

At a given time, at least one compound is added to the cell culture. The addition of the compound may be carried out at the beginning of myoblasts culture, during incubation of the myoblasts or once the myotubes are mature. The skilled person is able to select the appropriate time of addition of the compound depending on the goal of the assay.

After a determined incubation time of the myotubes with said compound, image analysis of the myotubes is carried out to determine the effect of said compound on the myotubes. The incubation time depends on the experimental protocol and on the cell type. This incubation time is typically comprised between 2 and 15 days, preferably between 2 and 6 days for human myotubes.

The standardization of the morphological parameters of the myotubes allows determining characteristic features of the myotubes in view of quantifying the effect of the tested compound. Indeed, the effect of the compound can be assessed by measuring morphological changes, such as size, diameter, thickness or width, induced by atrophy or hypertrophy in skeletal muscle cells and in particular myotubes or myoblasts.

Figure 14A:
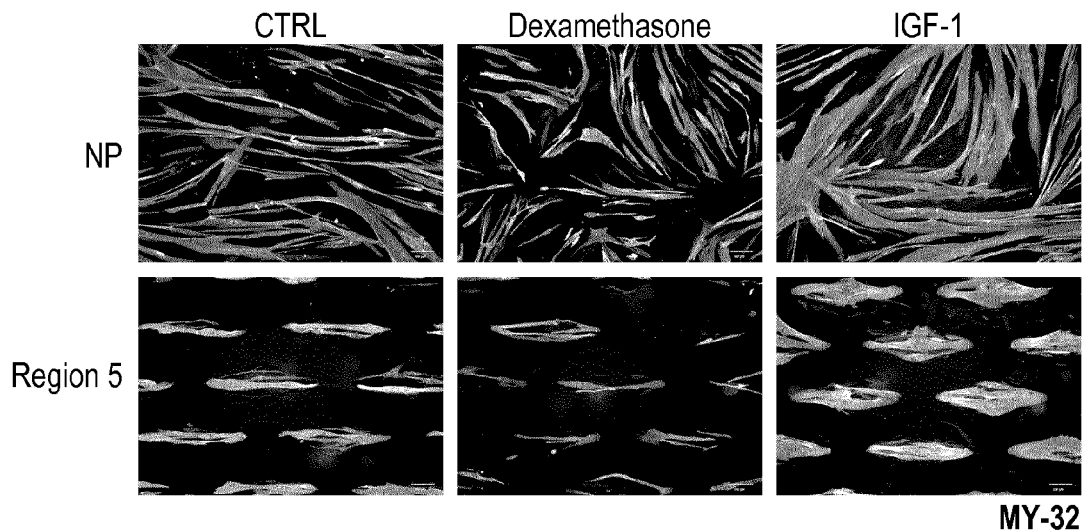
FIG. 14A shows representative micrographies of myotubes morphologies, from primary human myoblasts, in control conditions (CTRL, left) and after atrophic (dexamethasone, middle) and hypertrophic (IGF-1, right) compounds treatment during 72 hours on both unpatterned (NP) and micropatterned (according to the invention using the pattern of region 5 of FIG. 3, bottom) surfaces).

FIG. 14A shows representative myotubes after atrophic and hypertrophic reference compound treatment (respectively dexamethasone and IGF-1) on both unpatterned (NP) surface and Region 5 patterns. Human primary myoblasts (HSMM, Lonza) are cultured on fibronectin coated surfaces within growth medium (Lonza SkGM™-2 cell culture Kit) during 24 hours. Then cells are cultured within differentiation medium (DMEM/F12, 2% Horse Serum, 0.5% P/S) for 24 hours. Compounds (dexamethasone 100 µM and IGF-1 15 nM concentration) are added to the forming myotubes during 72 hours. Cells are fixed and an immunostaining is realized against myosin heavy chain, myogenin and nuclei. Images are acquired using an Operetta high content imaging system (PerkinElmer).

In order to characterize compounds mode of action on the myotube model (including myoblasts differentiation, myotube maturation, myotube hypertrophy, myotube atrophy, or cell viability), automated image segmentation and analysis methods has been developed by the inventors using the Acapella software library (Perkin Elmer).

First, customized segmentations of myotubes and nuclei are performed.

Then, objects are analyzed to extract basic parameters such as myotube count, nuclei count, myotube morphology (including their length, width, area, and orientation), fusion index (through the percentage of myogenin containing nuclei). Taking said parameters into account, aberrant myotubes are removed.

Finally, an advanced descriptor is measured, called "maximal width readout", which is the highest value of the internal distance map within remaining myotubes.

By "distance map" is meant the result of an image process involving "distance transform" operation realized after myotube image binarization, which assigns to each pixel the Euclidean distance to the nearest object border point. Distance maps are known in the art and will not need further description.

The percentage of high responders for this advanced descriptor was used to characterize the myotubes cultured in control and treated conditions for both NP and Region 5 patterns.

By "high responder" is meant the myotubes having a value, for one of the previously described descriptors, greater than a predetermined threshold.

Figure 14B:
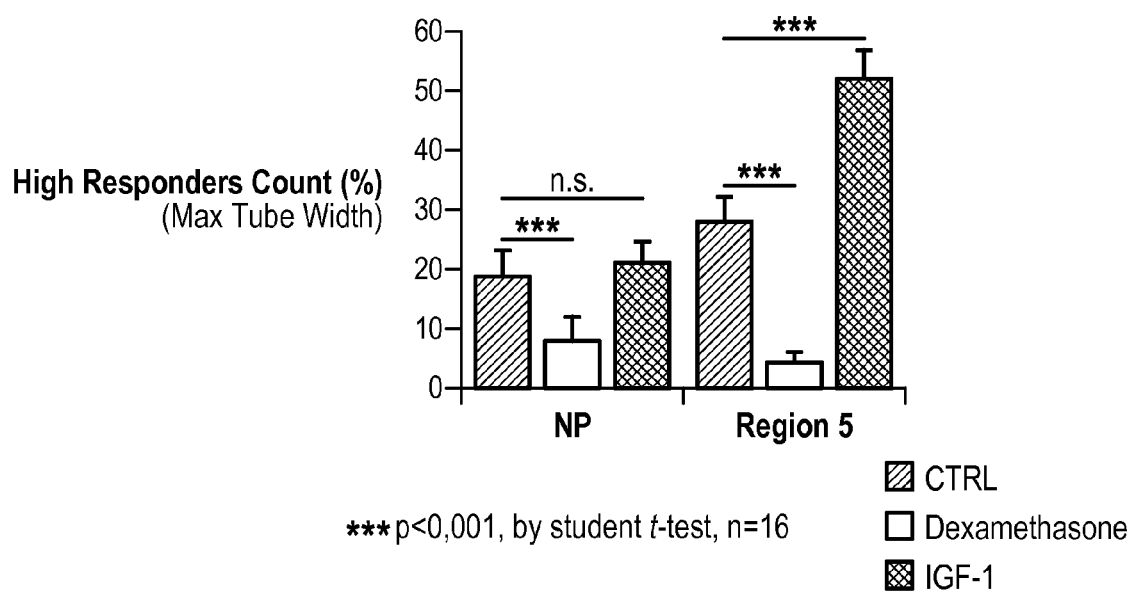
FIG. 14B is a quantification of the so-called high responder count of the Maximal Width readout of myotubes cultured in control and treatment conditions on NP and Region 5 patterns.

FIG. 14B is a representative result of the image processing. The patterns according to the invention provide a large increase of the assay window between control and treated conditions for both atrophic (+144%) and hypertrophic (+733%) treatments as compared to unpatterned surfaces.

Together with the provided standardization, this increase in assay window validates the compatibility of the invention with compounds screening (Z'-factors upper than 0.2).

Example

The invention was used in a proof of principle screen with selected compounds (10 µM concentration) known for their myotoxic activity.

In this screening method, human primary myoblasts (HSMM, Lonza) are cultured on fibronectin coated surfaces (Region 5 patterns) within growth medium (Lonza SkGM™-2 cell culture Kit) during 24 hours. Then cells are cultured within differentiation medium (DMEM/F12, 2% Horse Serum, 0.5% P/S) for 24 hours. 60 different compounds, known as inducers of myotoxicity (including rhabdomyolysis syndromes, lysosomal myopathies, myofibrillar myopathies, inflammatory myopathies, hypokalemia myopathies, corticosteroid myopathies, myositis, myosin deficiency) and control, are added to the forming myotubes during 72 hours. Cells are fixed and an immunostaining is realized against myosin heavy chain, myogenin and nuclei. Images are acquired using an Operetta high content imaging system (Perkin Elmer).

High responders, i.e. myotubes having a maximal width greater than a predetermined threshold, are counted.

As a result, 40% to 70% of compounds inducing myopathies are detected myotoxic. More precisely, most of the statin drug family members are detected (6 of the 7 tested) by using the present invention, compared to 1 when using a standard tissue culture device with an unpatterned surface.

REFERENCES

[Abmayr 2012] S. M. Abmayr et al, Myoblast fusion: lessons from flies and mice, Development 139, 641-656 (2012)

[Junkin 2011] M. Junkin et al, Cellular self-organization by autocatalytic alignment feedback, Journal of Cell Science 124, 4213-4220 (2011)

[Yamamoto 2008] D. L. Yamamoto et al, Myotube Formation on Micro-Patterned Glass: Intracellular Organization and Protein Distribution in C2C12 Skeletal Muscle Cells, J. Histochem. Cytochem 56, 881-892 (2008)

[Bajaj 2011] P. Bajaj et al, Patterning the differentiation of C2C12 skeletal myoblasts, Integrative Biology 3, 897-909 (2011)

[Engler 2004] A. J. Engler et al, Myotubes differentiate optimally on substrates with tissue-like stiffness: pathological implications for soft or stiff microenvironments, Journal of Cell Biology, Vol. 66, No. 6, 877-878 (2004)

[Engler 2008] A. J. Engler et al, Embryonic cardiomyocytes beat best on a matrix with heart-like elasticity: scar-like rigidity inhibits beating, Journal of Cell Science 121 (22), 3794-3802 (2008)

[Tseng 2011] Q. Tseng et al, A new micropatterning method of soft substrates reveals that different tumorigenic signals can promote or reduce cell contraction levels, Lab on Chip 7, 2231-2240 (2011)

[Polio 2012] S. R. Polio et al, A micropatterning and image processing approach to simplify measurement of cellular traction forces, Acta Biomaterialia 8, 82-88 (2012)

[Serena 2010] E. Serena et al, Soft substrates drive optimal differentiation of human healthy and dystrophic myotubes, Integr. Biol., 2010, 2, 193-201

[Zatti 2010] E. Zatti et al, Soft substrates drive optimal differentiation of human healthy and dystrophic myotubes, Integrative Biology 2, 193-201 (2010)

[Cimetta 2009] E. Cimetta et al, Production of arrays of cardiac and skeletal muscle myofibers by micropatterning techniques on a soft substrate, Biomed Microdevices (2009) 11:389-400

[Monge 2012] C. Monge et al, Engineering muscle tissues on microstructured polyelectrolyte multilayer films, Tissue Eng. Part A 2012, 18(15-16): 1664-76 US 2011/0189719

[Strochlic 2012] L. Strochlic et al, Wnt4 participates in the formation of vertebrate neuromuscular junction, PLoS One 7, e29976 (2012)

[Wang 2008] J. Wang et al, Wnt/beta-catenin signaling suppresses Rapsyn expression and inhibits acetylcholine receptor clustering at the neuromuscular junction, J Biol Chem 283, 21668-21675 (2008)

The invention claimed is:

1. A device for controlling myoblast differentiation into myotubes with standardized morphological parameters, comprising a substrate and at least one cell-adhesive pattern for culturing myoblasts on said substrate, wherein:
    said pattern has an elongated surface comprising a central region and two lateral regions extending from said central region in both directions along a longitudinal axis of the pattern with a contour discontinuity between the central region and each lateral region, a length of the pattern being between 100 and 1000 µm and a maximum width of said pattern being between 50 and 500 µm,
    a ratio between a maximum width of the central region and a maximum width of the lateral regions is greater than or equal to 2,
    a ratio between the length and the maximum width of the pattern is less than or equal to and
    wherein the pattern consists of three elliptical surfaces partially superimposed in the central region of the pattern:
    a first elliptical surface defining the central region of the pattern; and
    second and third elliptical surfaces having a major axis coinciding with a major axis of the first ellipse defining the lateral regions of the pattern,
    wherein the second and third elliptical surfaces intersect the first elliptical surface along their transversal axis.

2. The device according to claim 1, wherein the pattern is symmetrical according to its longitudinal axis and to a transversal axis perpendicular to the longitudinal axis.

3. The device according to claim 1, wherein the ratio between the length and the maximum width of the pattern is 2.5.

4. The device according to claim 1, wherein the area of said pattern is between 5,000 and 500,000 µm².

5. The device according to claim 1, wherein the substrate is a hard substrate.

6. The device according to claim 1, wherein the substrate is a soft substrate.

7. The device according to claim 6, wherein the Young's modulus of the substrate is comprised between 5 and 15 kPa.

8. A method for promoting myoblast differentiation into myotubes, comprising:
    (i) providing a device according to claim 1,
    (ii) depositing myoblasts on at least one cell-adhesive pattern of said device, and,
    (iii) culturing said myoblasts in a differentiation medium during a determined incubation time so as to promote cell differentiation into striated myotubes, and constrain elongation of the myotubes on the cell-adhesive pattern.

9. The method according to claim 8, wherein the myoblasts are primary myoblasts from donors, cell lines or isogenic cell lines or are stem cell derived myoblasts.

10. A method for screening compounds driving changes in myotubes, comprising:
    (i) providing a device according to claim 1,
    (ii) depositing myoblasts on at least one cell-adhesive pattern of said device,
    (iii) culturing said myoblasts in a differentiation medium so as to promote cell differentiation into myotubes,
    (iv) adding at least one compound to said culture, and,
    (v) carrying out image analysis of the myotubes to determine the effect of said at least one compound on the myotubes by measuring morphological changes of the myotubes.

11. The method according to claim 10, wherein said myoblasts are obtained from a healthy donor or from a cell line and wherein the image analysis is carried out to determine the effect of said compound in terms of myotoxicity by measuring myoblast differentiation, myotube maturation, myotube atrophy, myotube hypertrophy, and cytotoxicity defects of the myotubes myotubes.

12. The method according to claim 10, wherein said myoblasts are obtained from a donor suffering from a determined muscle related pathology or from cell line associated with a muscle related disease and weakness, and the image analysis is carried out to determine the effect of said compounds in terms of atrophic or hypertrophic properties.

13. The method according to claim 10, wherein said measured morphological changes comprise the maximal width of the myotubes after incubation with the compound and wherein image analysis comprises myotube image binarization, computation of a distance map of said myotubes and computation of the maximal width of each myotube from said distance map.

14. The method according to claim 13, further comprising counting the myotubes having a maximal width greater than a predetermined value.

* * * * *

UNITED STATES PATENT AND TRADEMARK OFFICE
CERTIFICATE OF CORRECTION

PATENT NO. : 10,711,248 B2
APPLICATION NO. : 15/105548
DATED : July 14, 2020
INVENTOR(S) : Mathieu Fernandes et al.

Page 1 of 1

It is certified that error appears in the above-identified patent and that said Letters Patent is hereby corrected as shown below:

In the Claims

<u>Column 13,</u>
Line 22, "or equal to and" should read --or equal to 4, and--.

Signed and Sealed this
Tenth Day of November, 2020

Andrei Iancu
*Director of the United States Patent and Trademark Office*